United States Patent [19]

Månsson et al.

[11] Patent Number: 5,576,345
[45] Date of Patent: Nov. 19, 1996

[54] METHOD AND MEANS FOR INHIBITING POSTERIOR CAPSULE OPACIFICATION

[75] Inventors: Per Månsson, Sollentuna; Wenche Rolfsen; Kerstin Wickström, both of Upsala, all of Sweden

[73] Assignee: Pharmacia & Upjohn AB, Upsala, Sweden

[21] Appl. No.: 553,529

[22] PCT Filed: Apr. 26, 1994

[86] PCT No.: PCT/SE94/00371

§ 371 Date: Feb. 26, 1996

§ 102(e) Date: Feb. 26, 1996

[87] PCT Pub. No.: WO94/25020

PCT Pub. Date: Nov. 10, 1994

[30] Foreign Application Priority Data

Apr. 28, 1993 [SE] Sweden .................................. 9301422

[51] Int. Cl.$^6$ .................................. A61K 31/335
[52] U.S. Cl. .................................. 514/449
[58] Field of Search .................................. 514/449

[56] References Cited

U.S. PATENT DOCUMENTS 5,252,319 10/1993 Babcock et al. ..................... 424/78.04

OTHER PUBLICATIONS

Chem. Abstract of Barza et al. (abstract No. 107:12808) 1987.

Chem. Abstract of Van Bockxmeer et al. (abstract No. 103:154095) 1985.

Graefe's Archive of Clinical and Experimental Ophthalmology, vol. 228, 1990, Stewart A. Daniels et al., "Taxol treatment of experimental proliferative vitreoretinopathy".

Ophthalmic Res, vol. 22, 1990, J. M. Ruiz et al., "Inhibition of Posterior Capsule Opacification by 5-Fluorouacil in Rabbits".

STN, EMBASE, Accession No. 93309059, Jampel H. D. et al: "Glaucoma filtration surgery in nonhuman primates using taxol and etoposide in polyanhydride carriers". Invest. Ophthalmol. Visual Sci., (1993)34/11 (3075–3083).

*Primary Examiner*—Raymond Henley, III
*Attorney, Agent, or Firm*—Dinsmore & Shohl

[57] ABSTRACT

The present invention is directed to the use of taxol or a pharmaceutically and ophthalmologically acceptable derivative thereof for the prevention of secondary cataracts after extracapsular extraction with or without intraocular lens implantation.

12 Claims, No Drawings

METHOD AND MEANS FOR INHIBITING POSTERIOR CAPSULE OPACIFICATION

This application is a 371 of PCT/SE94/00371 filed Apr. 26, 1994.

The present invention is related to the field of ophthalmology and more specifically to a composition and its use for preventing secondary cataract, a long term complication after extracapsular cataract extraction with or without intraocular lens (IOL) implantation.

A great number of intraocular lens models have been developed and commercialised over the years and these as well as the techniques for IOL implantation have been improved so that extracapsular cataract extraction with intraocular lens implantation are nowadays well established procedures with a high success rate. Opacification of the posterior capsule in the optical axis is however still a significant long-term complication reported, within 3 to 5 years after surgery, in as much as 50% of the cases. This condition is the result of deposition or in-growth of cells, mainly remnant lens epithelial cells (LEC) which proliferate on the posterior lens capsule resulting in blocking of incoming light. The direct consequence is the need for posterior capsultomy, which has a comparatively high incidence (1–3%) of serious complications.

A number of different ways to prevent secondary cataract have been tested over the years, both with regard to the intraocular lens as such and the technique used in surgery. So has for instance Hoffer in U.S. Pat. No. 4,244,060 described a lens that has a barrier ridge on the side facing the capsule wall. The intention is to create a mechanical barrier inhibiting migration of residual lens epithelial cells and their derivatives into the optical zone behind the IOL.

Administration of various types of drugs during surgery for preventing opacification is another approach that has been found to be of potential importance. Examples of such drugs are colchicine and 5-fluorouracil.

Colchicine is a mitosis-inhibiting phenanthrene derivative isolated from *Colchicum autumnale*. Colchicine arrests mitosis at metaphase by binding to a protein present in microtubules, hence interfering with the structure of the mitotic spindle. The substance has been shown to be a potent inhibitor of lens epithelial cell proliferation and migration. However, colchicine has a low therapeutic index with a lot of potential side effects, including a temporary toxic effect on the optic nerve when used for preventing posterior capsule opacification in primates.

5-Fluorouracil is a potent anti mitotic drug affecting the DNA replication and is widely used in the treatment of epithelial tumours. Ruitz et al (Inhibition of posterior capsule opcification by 5-fluorouracil in rabbit; Ophthalmic Res. 22 (1990) 201–208) have also shown that this substance reduces posterior capsule opacification in vive in rabbits.

Since 1982 subconjunctival administration of 5-fluorouracil has been utilized in patients at high risk of failure of glaucoma filtering surgery. Although beneficial effects of the substance have been clearly demonstrated, disadvantages have included corneal epithelial defects and other ocular complications.

In spite of the different approaches tested, opacification is still a considerable problem. We have now found that the substance taxol that is obtained from the bark of Western yew (*Taxus brevifolia*) constitutes a very promising drug candidate for preventing opacification after extracapsular cataract extraction. The substance is known to promote the formation of microtubule bundles, which deform the cytoskeleton and interfere with mitosis. Taxol is used as a broad spectrum antitumour agent in many different forms of tumours.

Chemical as well as certain therapeutic properties of taxol and some derivatives of taxol have been described in the literature, see for instance "The Chemistry of Taxol, a Clinically Useful Anticancer Agent" by Kingston et al in Journal of Natural Products 53(1) (1990) pages 1–12. With taxol derivatives for use according to the invention is meant functional analogues which are effective in preventing secondary cataract by inhibiting epithelial cell proliferation and migration. In the article by Kingston et al various derivatives are disclosed and these are included here by reference.

Taxol has also been tested in certain ophthalmological applications. Joseph et al (Current Eye Research 8(2) (1989) p.203–215) have suggested its potential use in glaucoma drainage surgery and taxol has also been found useful in inhibiting tractional retinal detachment in experimentally induced proliferative vitreoretinopathy in the eyes of rabbits (see Daniels et al, Graefe's Arch Clin Exp Ophthalmol 228 (1990) p.513–516). Because of the poor solubility in aqueous solution taxol was dissolved in 30% dimethylsulfoxide (DMSO).

Daniels SA et al (Ocular Toxicity of Intravitreal Taxol; J Toxicol & Ocular Toxicol 8 (1989) p 191–199) have suggested that up to about 8.5 µg of taxol in 0.1 ml of solution can safely be injected as single intravitral doses in rabbit's eyes without causing damage to the ocular tissue.

The method of preventing opacification after extracapsular cataract extraction comprises the administration of a small amount of taxol in a single dose during surgery. The substance is administered in solid state, for instance in microcrystalline form or dissolved in an ophthalmologically acceptable medium. It is also possible to dissolve the substance in one medium, in which the solubility is good, with subsequent transfer of the dissolved substance to a carrier matrix as described below, whereby the medium used for dissolving the substance is removed. This procedure makes it possible to use as a solubilizing agent a medium which is not well suited for use inside the eye. Examples of systems for solubilizing the active compound include alcohols like ethanol. After that the substance has been transferred to the carrier medium or matrix the solvent is removed for instance by evaporation or simply washed away.

In a first embodiment of the invention taxol or a derivative thereof is administered in a small volume, for instance 0.1 to 0.3 ml, of a viscoelastic medium of a type that is ophthalmologically acceptable, for instance aqueous solutions of hyaluronic acid or carboxymethyl cellulose, just to mention a couple of examples. The most widely used substance in this connection is Healon®, a highly purified hyaluronic acid product from Kabi Pharmacia AB. In most cases the viscoelastic medium that has been used for facilitating the surgical procedure is removed and after this has been done the taxol-containing volume is injected into the space between the lens and the capsule wall, and the opening in the eye is closed.

In a second embodiment of the invention taxol, or a derivative thereof, is incorporated in an intraocular drug delivery system providing a slow release effect. The active substance in solid form could be coated with or encapsulated by an ophthalmologically acceptable carrier substance. Examples of systems, which are generally known for encapsulating drugs, are liposomes which are membranelike vesicles, and microspheres based on polymers of lactic and glycolic acid. A slow release system can alternatively be prepared by adding taxol or derivative thereof in dissolved form to a carrier matrix under conditions so that a desired amount of the substance is incorporated. An example of such a carrier matrix is a gel, for instance a biodegradable gel of hyaluronic acid as disclosed in EP 408731.

In a third embodiment of the invention the intraocular lens to be implanted is used as carrier for taxol or the derivative thereof, for instance adsorbed or bound to the lens surface, preferably to the haptics, or as a slow-release depot in a hole or cavity outside the optical part of the lens surface.

In a fourth embodiment of the invention a slow release composition comprising taxol or a derivative thereof is deposited directly on the capsule tissue, under conditions so that the composition is bound to the tissue or forms an interpenetrating network with the tissue surface layer.

In a relevant in vitro test that has been carried out, rabbit lens epithelial cells were exposed to a series of taxol solutions with various concentrations for about one week in culture. The substance was dissolved in absolute ethanol and was then diluted with the culture medium (Dulbecco's Modified Eagle Medium supplemented with Ham's F-12, antibiotics and foetal calf serum) to concentrations in the range of from 1 pg/ml to 1 mg/ml. At concentrations exceeding 100 ng/ml significant reduction in cellular growth was observed, confirming the potential use of taxol and ophthalmologically active derivatives thereof for preventing secondary cataract.

The at present preferred embodiment of the invention comprises intraocular administration of taxol in microcrystalline form in an amount of about 0.005 to 5 µg and especially 0.1 to 5 µg, in approximately 0.1 ml of a viscoelastic medium, especially Healon®. The dose might especially in slow release systems be considerably higher, for instance up to about 25 µg.

We claim:

1. A method for preventing secondary cataract after extracapsular cataract extraction, comprising administering taxol or a pharmaceutically active and ophthalmologically acceptable derivative thereof to the intraocular area after extracapsular cataract extraction.

2. A method as defined by claim 1, wherein an intraocular lens is implanted in the intraocular area before, simultaneous with or after said administration.

3. A method as defined by claim 1, wherein no intraocular lens is implanted in the intraocular area before, simultaneous with or after said administration.

4. A method as defined by claim 1, wherein the taxol or the derivative thereof is administered in an amount of up to 25 µg.

5. A method as defined by claim 1, wherein the taxol or the derivative thereof is administered in an amount of from about 0.005 to 5 µg.

6. A method as defined by claim 1, wherein the taxol or the derivative thereof is administered in an amount of from 0.1 to 5 µg.

7. A method as defined by claim 1, wherein the taxol or the derivative thereof is administered in a microcrystalline form.

8. A method as defined by claim 1, wherein the taxol or the derivative thereof is administered in a slow release composition.

9. A method as defined by claim 1, wherein the taxol or the derivative thereof is administered in an ophthalmologically acceptable viscoelastic medium.

10. A method as defined by claim 9, wherein the viscoelastic medium comprises an aqueous solution of hyaluronic acid.

11. A method as defined by claim 9, wherein the visoelastic medium is administered in an amount of from 0.1 to 0.3 ml.

12. A method as defined by claim 1, wherein the taxol or a pharmaceutically active and opthalmologically acceptable derivative thereof is administered in microcrystalline form in an amount of about 0.005 to 5 µg in approximately 0.1 ml of an aqueous hyaluronic acid solution.

* * * * *